(12) United States Patent
Yeh

(10) Patent No.: US 7,026,137 B2
(45) Date of Patent: Apr. 11, 2006

(54) HEPATITIS

(75) Inventor: Chau-Ting Yeh, Taipei (TW)

(73) Assignee: Chang Gung University, Taoyuan (TW)

( * ) Notice: Subject to any disclaimer, the term of this patent is extended or adjusted under 35 U.S.C. 154(b) by 0 days.

(21) Appl. No.: 10/956,750

(22) Filed: Oct. 1, 2004

(65) Prior Publication Data

US 2005/0084847 A1    Apr. 21, 2005

Related U.S. Application Data

(62) Division of application No. 10/688,302, filed on Oct. 15, 2003, now Pat. No. 6,852,505.

(51) Int. Cl.
*C12Q 1/66* (2006.01)
*C12Q 1/70* (2006.01)
*C12Q 1/68* (2006.01)
*G01N 33/48* (2006.01)
*G01N 33/532* (2006.01)
*G01N 33/544* (2006.01)
*G01N 33/543* (2006.01)
*G01N 33/483* (2006.01)

(52) U.S. Cl. .................. 435/32; 435/33; 435/40.51; 435/40.42; 435/40.5; 435/41; 435/34; 435/4; 435/5; 435/6; 435/7; 435/91.1; 435/188

(58) Field of Classification Search .................. 435/32, 435/40.5, 40.51, 40.52, 34, 41, 4, 5, 6, 7
See application file for complete search history.

(56) References Cited

OTHER PUBLICATIONS

Chayama et al. Hepatology 1998, vol. vol. 27, No. 6, pp. 1711-1716.*
Clercq De Eric International Journal of Antimicrobial Agents 1999, vol. 12, pp. 81-95.*
Matsuda et al. J. Medical, Virol. 2004, vol. 74, pp. 361-366*
Vuillermoz et al. J Med Virol. Sep. 2004;74(1):41-53.*
Lu et al. Antimicrob Agents Chemother. Jun. 2004;48(6):2260-6).*
Nguyen et al. Antimicrob Agents Chemother. Nov. 2003;47(11):3525-30.*
Purcell R. Hepatology 1997, vol. 26, pp. 11S-14S.*

* cited by examiner

*Primary Examiner*—James Housel
*Assistant Examiner*—Bao Qun Li
(74) *Attorney, Agent, or Firm*—Fish & Richardson P.C.

(57) ABSTRACT

A screening method of identifying a compound for treating hepatitis. Also disclosed is a method for evaluating responsiveness of a subject having hepatitis to a drug.

13 Claims, No Drawings

HEPATITIS

RELATED APPLICATIONS

This application is a divisional application and claims priority to U.S. application Ser. No. 10/688,302, filed Oct. 15, 2003, now issued as U.S. Pat. No. 6,852,505, the contents of which are incorporated herein by reference.

BACKGROUND

Hepatitis can be caused by many infection agents, including hepatitis A, B, C, D, and E viruses and GB virus.

Viral hepatitis is the single most important cause of liver disease. Take hepatitis C for example, it is estimated to affect 170 million people worldwide. Patients with liver damage resulting from hepatitis C may develop chronic liver diseases, such as cirrhosis and hepatocellular carcinoma. Hepatitis C can be treated with interferon α. However, only about 50% hepatitis C patients are responsive to the treatment. Other drawbacks to interferon α therapy include significant side effects, high costs, and poor responsiveness to hepatitis C virus genotype 1, the most common genotype in the United States. New therapies have being vigorously sought. Although several drug candidates are now being evaluated, the progress is rather slow due to a lack of appropriate animal models and uncertainty of responsiveness in humans.

Thus, there is a need for a reliable method for identifying drugs for treating hepatitis C and other viral hepatitis.

SUMMARY

This invention is based, at least in part, on an unexpected discovery that hepatitis virus replicates in vitro in human liver slices. Liver slices infected with hepatitis virus can thus be used to screen compounds for treating hepatitis.

One aspect of the invention features a screening method of identifying a compound for treating hepatitis. The method includes (1) obtaining a first liver slice from a subject having hepatitis; (2) incubating the first liver slice in a medium containing a compound; and (3) determining the replication level of a hepatitis virus, e.g., a hepatitis C virus, hepatitis B virus, hepatitis D virus, or GB virus, in the first liver slice. The compound is determined to be effective in treating hepatitis if the replication level of the hepatitis virus is lower than that determined in the same manner from a second liver slice except that the second liver slice is incubated in a medium free of the compound. The replication level of the hepatitis virus can be based on the replication rate, genome level, or protein level of the hepatitis virus. In a preferred embodiment, the method is used to identify a compound for treating hepatitis C. In this embodiment, the protein level of HCV can be that of core protein, E1 protein, E2 protein, p7 protein, NS3 protein, NS4A protein, NS4B protein, NS5A protein, NS5B protein, or F protein.

It is known that hepatitis patients respond differently to different anti-hepatitis drugs. The invention also features a method of evaluating responsiveness of a subject having hepatitis to a known drug. This method is identical to the method described above, except that a known drug, instead of a test compound, is used. The subject is determined to be responsive to the drug if the replication level of the hepatitis virus in the first slice is lower than that in the second slice. This method can be employed before, during, or after a therapy.

The details of one or more embodiments of the invention are set forth in the accompanying description below. Other advantages, features, and objects of the invention will be apparent from the detailed description and the claims.

DETAILED DESCRIPTION

This invention relates to the use of liver slices in identifying compounds in treating hepatitis.

For example, within the scope of this invention is a method for screening a compound that can be used in treating hepatitis. To practice the method, one incubates a compound in a medium with a liver slice prepared from a subject having hepatitis for a period of time, e.g., 24 to 96 hours, and then determines the replication level of the virus, such as genome level, protein level, or the replication rate of the virus, in the liver slice. One also determines a control replication level of the virus in a second liver slice in the same manner except that the second liver slice is incubated in a medium free of the compound. If the replication level in the first slice is lower than that in the second slice, the compound is a candidate for treating hepatitis.

A liver slice can be prepared using techniques well known in the art. It can be prepared in different dimensions and maintained in various culture systems. See, e.g., Groneberg et al., Toxicol. Pathol. 30 (2002) 394–399 and Ekins Drug Metab. Rev. 28 (1996) 591–623. A plurality of liver slices can be obtained from a subject and stored in, e.g., liquid nitrogen, for later use (Isachenko et al., Eur. J. Obstet. Gynecol. Reprod. Biol. Jun. 10, 2003; 108(2):186–93). These slices can also be used in parallel to screen different compounds, thereby achieving high-throughput screening.

The replication level of a virus can be determined using techniques described in the example below or using those known in the art. For example, the genome level can be determined using RT-PCR. To determine the level of a viral protein, one can use techniques including ELISA, immunoprecipitation, immunofluorescence, EIA, RIA, and Western blotting analysis. To determine the replication rate of a virus, one can use the method described in, e.g., Billaus et al., Virology 26 (2000) 180–188.

Compounds to be screened can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation), spatially addressable parallel solid phase or solution phase libraries, synthetic libraries obtained by deconvolution or affinity chromatography selection, the "one-bead one-compound" libraries, and antibody libraries. See, e.g., Zuckermann et al. (1994) J. Med. Chem. 37, 2678–85; Lam (1997) Anticancer Drug Des. 12, 145; Lam et al. (1991) Nature 354, 82; Houghten et al. (1991) Nature 354, 84; and Songyang et al. (1993) Cell 72, 767. Examples of methods for the synthesis of molecular libraries can be found in the art, for example, in: DeWitt et al. (1993) Proc. Natl. Acad. Sci. USA 90, 6909; Erb et al. (1994) Proc. Natl. Acad. Sci. USA 91, 11422; Zuckermann et al. (1994) J. Med. Chem. 37, 2678; Cho et al. (1993) Science 261, 1303; Carrell et al. (1994) Angew. Chem. Int. Ed. Engl. 33, 2059; Carell et al. (1994) Angew. Chem. Int. Ed. Engl. 33, 2061; and Gallop et al. (1994) J. Med. Chem. 37,1233. Libraries of compounds may be presented in solution (e.g., Houghten (1992) Biotechniques 13, 412–421), or on beads (Lam (1991) Nature 354, 82–84), chips (Fodor (1993) Nature 364, 555–556), bacteria (U.S. Pat. No. 5,223,409), spores (U.S. Pat. No. 5,223,409), plasmids (Cull et al. (1992) Proc. Natl. Acad. Sci. USA 89, 1865–1869), or phages (Scott and Smith (1990) Science 249, 386–390; Devlin (1990) Science 249, 404–406; Cwirla et al. (1990) Proc. Natl. Acad. Sci. USA 87, 6378–6382; Felici (1991) J. Mol. Biol. 222, 301–310; and U.S. Pat. No. 5,223,409).

Compounds to be screened can be known drugs that are used to treat other diseases. Those that are found to inhibit hepatitis virus replication in liver slices can be used in treating hepatitis. Screening known drugs is advantageous, since the toxicity, pharmacokinetics, and side effects data of the drugs are available and all ethical issues have already been solved. The only remaining issue is whether the drugs are effective in treating hepatitis. Take sodium stibogluconate for example. A compound of pentavalent antimony, it has been used to treat kala-azar as the first-line medicine for more than 50 years (Herwaldt et al., Am. J. Trop. Med. Hyg. 46 (1992) 296–306). It is administered by intravenous or intramuscular injection at a daily dose of 20 mg/kg for 28 days. As shown in the example below, this drug suppresses hepatitis C virus (HCV) replication in liver slices obtained from hepatitis C patients. As the effective blood concentration of this drug for inhibiting HCV replication, e.g., 100 μg/ml, is much lower than what is needed for treating kala-azar (400 μg/ml), the drug is expected to be safe in treating hepatitis C.

The invention also features a method of evaluating an individual's responsivenss to an anti-hepatitis drug. Hepatitis patients show different responsiveness to a therapy. For example, interferon-based therapies can only achieve a sustained virological response in about 50% of HCV patients (McHutchison et al., Clin. Liver Dis. 7 (2003) 149–161). As the above-described screening method is based on liver slices prepared from individual subjects, it can be used to examine the responsiveness of a patient to a drug and thereby determine whether the drug is suitable for treating that patient.

To evaluate a subject's responsiveness to different drugs, one prepares a number of liver slices from the subject and incubates them with the drugs, respectively. One then obtains the replication level of the virus in each of the liver slices and compares it to a control level in the manner described above. The subject is determined to be responsive to the drug if the replication level in a slice incubated with a drug is lower than the control level. This method can be used to monitor a hepatitis treatment in a subject. For this purpose, liver slices are prepared from a subject before, during, and after undergoing treatment. The slices are then subjected to the treatment in vitro, and the replication level of the virus in each slice is obtained in the manner described above. The subject is determined to have developed resistance to treatment, if the viral replication level in liver slices prepared during or after the treatment is higher than that in slices prepared before the treatment. Such information is useful in prognostication for hepatitis. It also assists clinicians in designing other therapies.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Patients

Under informed consent, biopsy samples were obtained from 5 groups of patients (i.e., Groups I-V). Each patient was tested for presence of anti-HCV antibody ("Anti-HCV") and hepatitis B surface antigen ("HBsAg"), the alanine aminotransferase activity ("ALT"), the knodell histology activity index ("HAI"), the viral genotype ("Genotype"), and the serum HCV-RNA concentration ("Concentration") using standard techniques. The basic information for each patient was listed in Table below.

TABLE

| Patients | Sex | Age (year) | Anti-HCV | HBsAg | ALT (Unit/Liter) | HAI score | Genotype | Concentration ($10^6$ copies/ml) |
|---|---|---|---|---|---|---|---|---|
| Group I. Biopsy tissues treated with IFN | | | | | | | | |
| IFN-1 | M | 37 | P | N | 698 | 7 | 1b | <0.01 |
| IFN-2 | F | 49 | P | N | 101 | 7 | 2b | 20.35 |
| IFN-3 | M | 37 | P | P | 111 | 5 | 2a | <0.01 |
| IFN-4 | M | 54 | P | N | 47 | 5 | 1b | 1.70 |
| IFN-5 | F | 48 | P | P | 370 | 8 | 1b | 31.01 |
| IFN-6 | F | 40 | N | P | 282 | 5 | — | — |
| Group II. Biopsy tissues treated with inactivated IFN | | | | | | | | |
| iIF-1 | M | 51 | P | N | 147 | 3 | 1b | 39.01 |
| iIF-2 | M | 47 | P | N | 368 | 8 | 1b | 45.51 |
| iIF-3 | F | 52 | P | N | 326 | 11 | 1b | 2.82 |
| iIF-4 | M | 53 | P | P | 112 | 4 | 2a | <0.01 |
| iIF-5 | M | 47 | N | P | 633 | 8 | — | — |
| iIF-6 | F | 60 | P | P | 121 | 9 | 2a | 2.90 |
| Group III. Biopsy tissues treated with 10 μg/ml of Stibogluconate | | | | | | | | |
| S10-1 | F | 52 | P | N | 253 | 6 | 1b | 0.49 |
| S10-2 | M | 39 | P | N | 125 | 6 | 2a | 0.07 |
| S10-3 | F | 42 | WP | N | 23 | 3 | 1b | <0.01 |
| S10-4 | M | 40 | P | N | 63 | 1 | 2a | <0.01 |
| S10-5 | M | 42 | N | P | 58 | 9 | — | — |
| S10-6 | M | 53 | N | N | 949 | 4 | 1b | 0.15 |
| Group IV. Biopsy tissues treated with 100 μg/ml of Stibogluconate | | | | | | | | |
| S00-1 | F | 52 | P | N | 145 | 8 | 2b | 41.01 |
| S00-2 | M | 56 | P | N | 89 | 3 | 1b | <0.01 |
| S00-3 | M | 43 | P | N | 39 | 7 | 1b | <0.01 |
| S00-4 | F | 55 | P | N | 90 | 10 | 2a | 0.85 |
| S00-5 | F | 44 | P | N | 88 | 7 | 1b | 45.30 |
| S00-6 | M | 25 | P | N | 75 | 3 | 1b | 98.33 |
| Group V. Biopsy tissues used for viability tests | | | | | | | | |
| V-1 | F | 75 | P | N | 251 | 12 | 1b | 0.14 |
| V-2 | F | 76 | N | N | 253 | 4 | 2a | 3.50 |
| V-3 | M | 48 | P | N | 89 | 8 | 1b | 26.28 |
| V-4 | M | 47 | P | P | 112 | 10 | 2a | <0.01 |
| V-5 | F | 58 | P | N | 147 | 6 | 1b | <0.01 |
| V-6 | F | 38 | P | N | 134 | 5 | 1b | <0.01 |

All patients were positive for anti-HCV antibody except IFN-6, iIF-5, S10-5, S10-6, and V-2. Among these 5 patients, S10-6 and V-2 were positive for serum HCV-RNA and diagnosed as having acute hepatitis C. The other three patients were tested positive for hepatitis B surface antigen and diagnosed as having chronic hepatitis B, and were included as negative controls. No statistically significant difference was found among the five groups in sex, age, ALT activity, HAI score, viral genotype, or serum HCV-RNA concentration.

Liver Slices

Liver slices were prepared from liver tissues of the patients. To obtain the livers tissues, biopsy was performed using Bard Biopty-Cut biopsy needles (C. R. Bard, Inc. Covington, Ga.) with a diameter of 1.2 mm (18 gauge). Two equal-sized slices, 1 mm in thickness, were separated from each tissue. The remaining portion (main portion) of each tissue was subjected to pathological examination. The liver slices were incubated in a 24-well culture plate containing 2 ml of minimal essential medium-20% fetal bovine serum and fed with fresh medium daily.

Drug Evaluation

1. Sodium Stibogluconate Suppressed HCV Replication in Human Liver Slice

Sodium stibogluconate had been found capable of suppressing the replication of an HCV replicon in a HCV subgenomic RNA replicon system (Ava5; Apath; St. Louis, Mo.). To evaluate whether it suppresses the authentic HCV replication in liver slices, the liver slices from patients S10-1 to S10-6 and S00-1 to S00-6 were incubated with 0, 10, and 100 μg/ml of sodium stibogluconate (Wuhan Shengmao Corp., Hubei, China), respectively, 24 hrs after the slices had been cultured in vitro. The slices from patient S10-5 served as a negative control. Three days later (i.e., 96 hr after the slices were cultured), the level of HCV RNA in each slice was measured.

To detect the HCV-RNA level, one step RT-PCR (not nested) was performed in the manner described in Yeh et al., J. Gen. Virol. 78 (1997) 2761–2770. As a control, β-actin mRNA was measured simultaneously. 20 PCR cycles were performed, in which the amounts of the PCR products had not yet reached to a plateau. The primers used were described in Yeh et al., Oncogene 19 (2000) 5213–5220. The HCV-RNA was quantified according to a method comparable to the branched DNA method described in Yeh et al, J. Virol. Methods 65 (1997) 219–226. HCV genotypes were determined using Inno-Lipa HCV II kit (Innogenetics, Zwijndrecht, Belgium).

It was found that, at 10 μg/ml, sodium stibogluconate partially suppressed HCV replication in the slices from patients S10-1, S10-2, S10-4, and S10-6, but not in those from patient S10-3. At 100 μg/ml, it almost completely suppressed HCV replication in the slices from patients S00-1, S00-2, S00-3, and S00-5, but not in those from patients S00-4 and S00-6.

2. Sodium Stibogluconate Suppressed HCV Replication in 293EBNA-Sip-L Cell Line

To verify the ability of sodium stibogluconate to inhibit HCV replication, a 293EBNA-Sip-L cell line was used. This cell line, permissive for HCV infection and replication, had been established by expressing a cellular factor, Sip-L, in 293EBNA cells (Yeh et al., J. Virol. 75 (2001) 11017–11024). This cell line was maintained in a Dulbecco's modified Eagle's medium containing 10% fetal bovine serum, 250 μg/ml G418, and 150 μg/ml hygromycin B. The cells were infected with HCV. Briefly, cells in a 60-mm-diameter petri dish were incubated with a medium containing 5 μl of HCV-positive serum ($10^7$ copies of HCV-RNA/ml) for 12 hr. The cells were then incubated in a fresh medium without the serum.

At the second day after the HCV infection, 293EBNA-Sip-L cells were incubated with media containing 0, 1, 10, and 100 μg/ml of sodium stibogluconate, respectively. At the seventh day, the cells were harvested to determine the intracellular level of HCV-RNA. The cells were trypsinized and washed two times with a fresh medium by centrifugation. The supernatant of the second wash (as a contamination control) and the washed cells were collected in pairs for RNA extraction and nested RT-PCR. A digoxigenin-labeled probe was used for the subsequent Southern blot analysis. The sequences of the primers, the method for generating the probe, and the procedure for RT-PCR were described in Yeh et al., J. Virol. 75 (2001) 11017–11024. An amplified HCV fragment was cloned into pCR2.1-TOPO (Invitrogen, Carlsbad, Calif.) to generate a plasmid, pTOPO-HCV5n, which served as a positive control in Southern blot analysis. As internal controls, the levels of 18s and 28s RNAs were measured.

Intracellular HCV-RNA in the cells not treated with sodium stibogluconate was found to be $2.31 \times 10^5$ per $10^5$ cells. In contrast, none was detected in cells treated with 1, 10, or 100 μg/ml of sodium stibogluconate using RT-PCR, which has a sensitivity of $<10^2$ copy per $10^5$ cells.

Sodium stibogluconate has been used in treating kala-azar at a daily dose of 20 mg/kg. The estimated blood concentration immediately after injection is about 400 μg/ml, much higher than an effective concentration found in this example (100 μg/ml). Thus, if the dosage used to treat kala-azar is given to hepatitis C patients, the drug concentrations can be maintained above effective level for over two half-lives. Furthermore, at a concentration as low as 10 μg/ml, sodium stibogluconate partially suppresses HCV replication. These indicate that sodium stibogluconate can be used to treat hepatitis C.

3. Responsiveness of Patients to Interferon-Alpha 2b

The responsiveness of patients to Interferon-alpha, a drug currently being used to treat hepatitis C, was evaluated using liver slices. Liver slices prepared from patients INF-1 to 6 were incubated with 5000 U/ml of interferon-alpha2b (Schering-Plough Corp., Kenilworth, N.J. Slices from patient IFN-6, who was infected by hepatitis B virus, were used as negative controls.

It was found that the HCV-RNA levels in the liver slices from patients IFN-1, 3, and 4 were suppressed to undetectable levels. Partial suppression was observed in the slices from patient IFN-5, and no suppression was seen in those from patient IFN-2. Judging from cell viability results and the β-actin levels in all slices, the differences in the responses to interferon-alpha were not due to cell damages or tissue sizes.

To prove that the interferon-alpha used was active, it was heated to 90° C. for 10 min before being incubated with the slices from patients iIF-1 to 6 in the same manner described above. The slices form patient iIF-5 served as negative controls. No suppression was found in these slices, indicating that the interferon-alpha was active.

4. Sodium Stibogluconate and Interferon-Alpha 2b each Protected Hepatocytes

To determine whether sodium stibogluconate or interferon-alpha 2b protects hepatocytes in human liver slices, the viability of hepatocytes in human liver slices incubated with the drugs was examined. As HCV replication causes the death of hepatocytes, intracellular aspartate aminotransferase (AST) leaks out. The intracellular level of AST therefore positively correlates with the cell viability.

Liver slices prepared from the patients in Group V were treated with sodium stibogluconate or interferon-alpha 2b in the manner described above. The AST activity in the medium was determined using a standard technique 48, 72, and 96 hrs after the slices had been cultured in vitro. The AST activities in a fresh medium and in the liver slices 96 hrs after incubation were also measured. For this purpose, the slices were homogenized using a mini-homogenizer (Pellet Pestles, Kimble Deltaware, Vineland, N.J). The percentages of AST leaked out to the medium and remained in the liver slices were calculated accordingly. The AST-leakage in the first 24 hr was measured as the liver cell damage at this stage was mostly caused by separation of the liver slices from the biopsy tissues.

It was found that, 96 hrs after the culture, the intracellular AST levels in cells incubated with sodium stibogluconate and interferon-alpha 2b decreased progressively to 72% and 83%, respectively. In cells not incubated with any drugs, the intracellular AST levels decreased to 57%. No significant difference was found between any two samples obtained at the same time-point. The results indicated that sodium stibogluconate and interferon-alpha 2b protected hepatocytes.

OTHER EMBODIMENT

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A screening method of identifying a candidate compound for treating a viral hepatitis, wherein said candidate compound is not a drug known to treat a viral hepatitis, the method comprising:
   obtaining a first liver slice from a subject having hepatitis;
   incubating the first liver slice in a medium containing said compound; and
   determining the replication level of a hepatitis virus in the first liver slice, incubating with said candidate compound
   wherein said candidate compound is determined to be effective for treating hepatitis if the replication level of the hepatitis virus is lower than that determined in the same manner from a second liver slice obtained and incubated in the same manner as the first liver slice except that the second liver slice is incubated in a medium free of the compound.

2. The method of claim 1, wherein the replication level of the hepatitis virus is based on the replication rate of the hepatitis virus.

3. The method of claim 1, wherein the replication level of the hepatitis virus is based on the genome level of the hepatitis virus.

4. The method of claim 1, wherein the replication level of the hepatitis virus is based on the protein level of the hepatitis virus.

5. The method of claim 1, wherein the hepatitis virus is a hepatitis C virus, hepatitis B virus, hepatitis D virus, or GB virus.

6. The method of claim 5, wherein the replication level of the hepatitis virus is based on the replication rate of the hepatitis virus.

7. The method of claim 5, wherein the replication level of the hepatitis virus is based on the genuine level of the hepatitis virus.

8. The method of claim 5, wherein the replication level of the hepatitis virus is based on the protein level of the hepatitis virus.

9. The method of claim 5, wherein the hepatitis virus is a hepatitis C virus.

10. The method of claim 9, wherein the replication level of the hepatitis virus is based on the replication rate of the hepatitis virus.

11. The method of claim 9, wherein the replication level of the hepatitis virus is based on the genome level of the hepatitis virus.

12. The method of claim 9, wherein the replication level of the hepatitis virus is based on the protein level of the hepatitis virus.

13. The method of claim 12, wherein the protein level is the level of the core protein, E1 protein, E2 protein, p7 protein, NS3 protein, NS4A protein, NS4B protein, NS5A protein, NS5B protein, or F protein of the hepatitis C virus.

* * * * *